(12) United States Patent
Williams

(10) Patent No.: US 11,793,547 B2
(45) Date of Patent: Oct. 24, 2023

(54) MEDICAL DEVICE, METHOD AND SYSTEM THEREOF

(71) Applicant: SOUTHWEST GYNMED, LLC, Flagstaff, AZ (US)

(72) Inventor: Phillip A. Williams, Flagstaff, AZ (US)

( * ) Notice: Subject to any disclaimer, the term of this patent is extended or adjusted under 35 U.S.C. 154(b) by 0 days.

(21) Appl. No.: 17/971,185

(22) Filed: Oct. 21, 2022

(65) Prior Publication Data
US 2023/0046038 A1 Feb. 16, 2023

Related U.S. Application Data

(63) Continuation of application No. 17/341,002, filed on Jun. 7, 2021, which is a continuation of application
(Continued)

(51) Int. Cl.
*A61B 17/34* (2006.01)
*A61B 1/313* (2006.01)
(Continued)

(52) U.S. Cl.
CPC ...... *A61B 17/3468* (2013.01); *A61B 1/00087* (2013.01); *A61B 1/3132* (2013.01); *A61B 5/686* (2013.01); *A61B 17/0469* (2013.01); *A61B 90/39* (2016.02); *A61B 90/98* (2016.02); *A61F 2/0063* (2013.01); *A61B 2017/00265* (2013.01);
(Continued)

(58) Field of Classification Search
CPC .. A61B 2017/00438; A61B 2090/3987; A61B 2017/0409; A61B 2017/0412; A61B 2017/042; A61B 2017/0427; A61B 2017/00265; A61B 17/3468; A61B 5/686; A61B 1/3132; A61B 1/00087; A61B 17/0469; A61B 90/98; A61B 90/39;
(Continued)

(56) References Cited

U.S. PATENT DOCUMENTS

| 2,006 | A | 3/1811 | Read |
| 195,007 | A | 9/1877 | Harkins |

(Continued)

FOREIGN PATENT DOCUMENTS

| CH | 641662 A5 | 3/1984 |
| WO | 0112084 A1 | 2/2001 |

(Continued)

OTHER PUBLICATIONS

AMI Agency for Medical Innovations, "A.MJ. EasyTac System," Prodcut Group Laparoscopy Issue Jan. 2005, 2 pages.
(Continued)

*Primary Examiner* — Christine H Matthews
*Assistant Examiner* — Joshua Daryl D Lannu
(74) *Attorney, Agent, or Firm* — Messner Reeves LLP; Scott J. Hawranek

(57) ABSTRACT

Embodiments of the invention are directed towards a medical device, method and system thereof for the placement or passage of patches, sutures, anchors, tags, tissue sensors and more particularly to a medical device for repairing female pelvic organ or tissue prolapsed region. The device may be used for the placement of stereotactic markers into tissue near joints or tumors for guidance during orthopedic or neurosurgical procedures.

23 Claims, 11 Drawing Sheets

Related U.S. Application Data

No. 16/251,953, filed on Jan. 18, 2019, now Pat. No. 11,026,720, which is a continuation of application No. 14/376,994, filed as application No. PCT/US2013/029197 on Mar. 5, 2013, now Pat. No. 10,182,843.

(60) Provisional application No. 61/607,411, filed on Mar. 6, 2012.

(51) Int. Cl.

| | | |
|---|---|---|
| *A61B 90/98* | (2016.01) | |
| *A61B 90/00* | (2016.01) | |
| *A61B 1/00* | (2006.01) | |
| *A61B 5/00* | (2006.01) | |
| *A61B 17/04* | (2006.01) | |
| *A61F 2/00* | (2006.01) | |
| *A61B 17/00* | (2006.01) | |

(52) U.S. Cl.
CPC ............... *A61B 2017/00438* (2013.01); *A61B 2017/00805* (2013.01); *A61B 2017/042* (2013.01); *A61B 2017/0409* (2013.01); *A61B 2017/0412* (2013.01); *A61B 2017/0427* (2013.01); *A61B 2090/397* (2016.02); *A61B 2090/3987* (2016.02); *A61F 2002/0072* (2013.01)

(58) Field of Classification Search
CPC ..... A61B 2090/397; A61B 2017/00805; A61F 2/0063; A61F 2002/0072
See application file for complete search history.

(56) References Cited

U.S. PATENT DOCUMENTS

| | | |
|---|---|---|
| 2,151,846 A | 3/1939 | Greneker |
| 2,704,889 A | 3/1955 | Delinanos |
| 2,707,828 A | 5/1955 | Stewart |
| 4,602,632 A | 7/1986 | Jorgensen |
| 4,726,371 A | 2/1988 | Gibbens |
| 4,892,520 A | 1/1990 | Gilbaugh |
| 5,079,629 A | 1/1992 | Oz |
| 5,152,293 A | 10/1992 | Vonesh et al. |
| 5,364,408 A | 11/1994 | Gordon |
| 5,448,989 A | 9/1995 | Heckele |
| 5,458,609 A | 10/1995 | Gordon et al. |
| 5,478,344 A | 12/1995 | Stone et al. |
| 5,522,788 A | 6/1996 | Kuzmak |
| 5,538,506 A | 7/1996 | Farris et al. |
| 5,540,704 A | 7/1996 | Gordon et al. |
| 5,549,637 A | 8/1996 | Crainich |
| 5,575,800 A | 11/1996 | Gordon |
| 5,578,044 A | 11/1996 | Gordon et al. |
| 5,662,664 A | 9/1997 | Gordon et al. |
| 5,700,272 A | 12/1997 | Gordon et al. |
| 5,713,910 A | 2/1998 | Gordon et al. |
| 5,741,277 A | 4/1998 | Gordon et al. |
| 5,741,279 A | 4/1998 | Gordon et al. |
| 5,746,998 A | 5/1998 | Torchilin et al. |
| 5,757,800 A | 5/1998 | Ishikawa et al. |
| 5,925,064 A | 7/1999 | Meyers et al. |
| 6,004,329 A | 12/1999 | Myers et al. |
| 6,048,351 A | 4/2000 | Gordon et al. |
| 6,332,888 B1 | 12/2001 | Levy et al. |
| 6,475,135 B1 | 11/2002 | Levy |
| 6,500,188 B2 | 12/2002 | Harper et al. |
| 7,338,502 B2 | 3/2008 | Rosenblatt |
| 7,347,812 B2 | 3/2008 | Mellier |
| D569,510 S | 5/2008 | Poll et al. |
| D569,511 S | 5/2008 | Poll et al. |
| D569,512 S | 5/2008 | Poll et al. |
| D569,513 S | 5/2008 | Poll et al. |
| D569,514 S | 5/2008 | Poll et al. |
| 7,582,096 B2 | 9/2009 | Gellman et al. |
| 7,789,878 B2 | 9/2010 | Dumbauld et al. |
| 7,790,141 B2 | 9/2010 | Pathak et al. |
| 7,828,189 B2 | 11/2010 | Holsten et al. |
| 7,828,798 B2 | 11/2010 | Buysse et al. |
| 2004/0199204 A1 | 10/2004 | Voegele et al. |
| 2004/0231167 A1 | 11/2004 | Miklos |
| 2004/0260281 A1 | 12/2004 | Baxter et al. |
| 2005/0131457 A1 | 6/2005 | Douglas et al. |
| 2005/0199249 A1 | 9/2005 | Karram |
| 2005/0251093 A1 | 11/2005 | Abou-Kansoul |
| 2006/0030884 A1 | 2/2006 | Yeung et al. |
| 2006/0036232 A1 | 2/2006 | Primavera et al. |
| 2006/0195007 A1 | 8/2006 | Anderson et al. |
| 2007/0073312 A1 | 3/2007 | Mykleby et al. |
| 2007/0088390 A1 | 4/2007 | Paz et al. |
| 2008/0009667 A1 | 1/2008 | Longhini et al. |
| 2008/0071208 A1 | 3/2008 | Voegele et al. |
| 2008/0167680 A1 | 7/2008 | Voegele et al. |
| 2008/0234543 A1 | 9/2008 | Goldwasser |
| 2009/0012353 A1 | 1/2009 | Beyer |
| 2009/0248046 A1 | 10/2009 | Primavera et al. |
| 2009/0259233 A1 | 10/2009 | Bogart et al. |
| 2010/0094083 A1 | 4/2010 | Taylor et al. |
| 2010/0147921 A1 | 6/2010 | Olson |
| 2010/0217282 A1 | 8/2010 | Cabrera et al. |
| 2010/0274265 A1 | 10/2010 | Wingardner et al. |
| 2011/0021869 A1 | 1/2011 | Cholhan |
| 2011/0040308 A1 | 2/2011 | Cabrera et al. |
| 2011/0092985 A1 | 4/2011 | Gaynor et al. |
| 2011/0092987 A1 | 4/2011 | Gaynor et al. |
| 2011/0092991 A1* | 4/2011 | Gaynor .............. A61B 17/0401 606/148 |
| 2011/0196389 A1 | 8/2011 | Schneider et al. |
| 2011/0270082 A1 | 11/2011 | Turner et al. |
| 2012/0283755 A1 | 11/2012 | Gellman et al. |
| 2015/0005586 A1 | 1/2015 | Williams |

FOREIGN PATENT DOCUMENTS

| | | |
|---|---|---|
| WO | 2007084411 A2 | 7/2007 |
| WO | 2013134313 A1 | 9/2013 |

OTHER PUBLICATIONS

Extended European Search Report issued in Application No. EP13757650.0, dated Jan. 8, 2016, 7 pages.

Goldberg., "Sacrospinous Ligament Suspension Using the CapioTM Suture Capture Technique," Touch Briefings, 2007, 4 pages.

Hiltunen R., et al., "Low-Weight Polypropylene Mesh for Anterior Vaginal Wall Proloapse," Obstetrics & Gynecology, 2007, vol. 110, pp. 445-462. Retrieved from URL http://www.greenjournal. Org/cgi/content/full/110/2/455.

International Preliminary Report on Patentability for International (PCT) Application No. PCT/US13/029197, dated Sep. 18, 2014, 10 pages.

International Search Report and Written Opinion for International (PCT) Application No. PCT/US13/29197, dated May 21, 2013, 11 pages.

Labeling: Regulatory Requirements for Medical Devices, FDA 89-4203, U.S. Department of Health and Human Services, Aug. 1, 1989, p. 16.

Position of Mesh, Retrieved from internet http://www.tvtsiing.com/images/position.-mesh.jpg on Sep. 13, 2007, 2 pages.

Teaching Brief—MedPage Today, "Bioabsorbable Magnesium Stent Shows ShortTenn Efficacy But Lacks Legs," Retrieved from Internet: https://www.medpagetoday.com/tbprint.cfintbid~5815 &topicid~306, on Sep. 20, 2007, 2 pages.

* cited by examiner

MEDICAL DEVICE, METHOD AND SYSTEM THEREOF

CROSS REFERENCE TO RELATED APPLICATIONS

This application is a continuation of U.S. application Ser. No. 17/341,002, filed Jun. 7, 2021, which is a continuation of U.S. application Ser. No. 16/251,953, filed Jan. 18, 2019, which is a continuation of U.S. application Ser. No. 14/376, 994, filed Aug. 6, 2014, which is a national stage application under 35 U.S.C. 371 of PCT Application No. PCT/US2013/029197 having an international filing date of 5 Mar. 2013, which designated the United States, which PCT application claimed the benefit of U.S. Provisional Application No. 61/607,411 filed 6 Mar. 2012, the entire disclosure of each of the foregoing are incorporated herein by reference in their entities.

BACKGROUND OF THE INVENTION

Field of the Invention

The invention generally relates to a medical device, method and system thereof for the placement or passage of patches, sutures, anchors, tags, tissue sensors and more particularly to a medical device for repairing female pelvic organ or tissue prolapsed region.

Discussion of the Related Art

It is estimated that nearly twelve percent of women will need surgery for pelvic organ prolapse. Historically, the long term result of these surgeries using the patient's own tissue for the repair, has been disappointing for both the patients and the surgeons. Recurrence of prolapse after standard autologous tissue repairs has been reported to be as high as about thirty percent to about forty percent.

Many current methods for pelvic reconstruction use instruments designed for laparoscopic surgery. These devices allow the surgeon to suture or anchor tissue, or to staple a patch or graft material into place. While laparoscopic instruments may be effective for laparoscopy when used under direct visualization, they tend to be less effective when used used in conditions of limited space and visualization, e.g., the vagina. More specifically, when laparoscopic instruments are used for vaginal surgery, there is a lack of tactile assistance or feedback when working from the end of an instrument. In addition, laparoscopic instruments are rigid and therefore not suited to the angles and planes encountered in vaginal surgery.

Methods, techniques and devices were developed that use a perineal approach. In these techniques, needles or carriers are placed through the skin of the perineum (outside the vagina) and into the pelvis and vagina. Once in position, graft material is attached to the needles which are drawn brought back out to the external skin, pulling the graft into position.

Moreover, these related art instruments are difficult to use with a perineal approach. Moreover, as the perineal approach is not widely taught, or familiar to many surgeons it is not a general skill of most surgeons, and it requires passage of a needle/carrier blindly through a great distance of tissue. Therefore, the difficulty of these techniques and related art devices limit their use to a very few specialists who are able to perform them, thereby limiting the availability of the treatment. Furthermore, this percutaneous approach has resulted in additional possible surgical complications, including infections, surrounding organ injuries, and painful scarring.

Other currently available methods and instruments available use a more traditional and familiar vaginal approach. These are generally sold as a kit, which include rigid devices used to aid in the attachment of graft materials. The graft is preformed and specific to the repair being done, i.e., anterior, posterior or apical. Currently available methods and instruments for the vaginal approach to prolapse repair utilize surgical skills and anatomical landmarks familiar to most gynecologists. However, the cost associated with the kits, the generally rigid and unwieldy nature of these devices render these kits problematic.

Therefore, there is a need for a device, method and/or system that addresses the above and other problems.

SUMMARY OF THE INVENTION

Accordingly, the invention is directed to a medical device, method and system thereof that substantially obviates one or more of the problems due to limitations and disadvantages of the related art.

An advantage of the invention is to provide a flexible finger-tip medical device for treatment that is configured to provide tactile feedback.

Another advantage of the invention is to provide a modular medical device that provides one robust tool allowing for different modular heads, e.g., visualization head, suture head, staple head, tag head, and combinations thereof.

Yet another advantage of the invention is to provide a device where a user not under visual would be able to locate the operating end based on orientation with one or more fingers.

Still yet another advantage of the invention is a medical device having stability of the and alignability along an axis of one or more of finger, hand, and arm, thereby allowing a using to accurately orient the operable end without the need of direct visualization.

Yet still another advantage of the invention is to provide a direct way to secure sutures and anchors in the vaginal approach to female pelvic organ prolapse repair.

Another advantage of the invention is its simplicity when used with a button or latch mechanism to deploy the anchor or tag.

Yet still another advantage of the invention is to provide a medical device with tactile feedback.

Another advantage of the invention is providing a flexible wire, flexible shaft, or other flexible mechanism allowing it to be used through small incisions and placed anywhere the fingertip can reach, not limited by a rigid or thick shaft.

Additional features and advantages of the invention will be set forth in the description which follows, and in part will be apparent from the description, or may be learned by practice of embodiments of the invention. The objectives and other advantages of the invention will be realized and attained by the structure particularly pointed out in the written description and claims hereof as well as the appended drawings.

One embodiment is directed towards a device having a two finger sheath and having at least one open finger, thereby allowing the user to have tactile dexterity to effectively map the surgical area by finger tip. The two finger sheath provides stability of the device and alignability of the device along an axis of the hand or arm. Other embodiments include at least one closed end finger sheath to allow the user to effectively and precisely secure an anchor to the patient.

In other embodiments, the sheath may be configured to only one finger, two fingers or three fingers. Still other embodiments include releasable attached devices to the sheaths which can assist the user in placing sutures.

In other embodiments, the device includes a kit, which contains at least two finger sheaths, a shaft or cable, a cylinder, a tapered ridge, and anchors and/or sutures.

In still another embodiment, the device is configured to allow a user to ascertain the force of placement of an anchor, suture, tag or other mechanism. In yet another embodiment, a viewing instrument maybe attached to the device to provide active visualization.

Yet still another embodiment is directed towards a tubular member having a lumen extending from a proximal end to a distal end, a finger assembly releasably coupled to a distal portion of the tubular member, an operating unit, directions for use and one or more of sutures, anchors, and the like. The finger assembly includes a first finger slot and second finger slot.

Still another embodiment is directed towards a method for using the device. The method allows the user to map the surgical region using at least one exposed finger. The user can then use the device to place anchors by way of an incision, e.g., a vaginal incision. In one embodiment, the anchors can be placed into ligaments located in the pelvis. The user may repair the pelvic organ prolapse or weakened vaginal tissues using a graft and anchors and/or sutures, or may do the repair using only anchors and/or sutures and the patient's own tissues.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
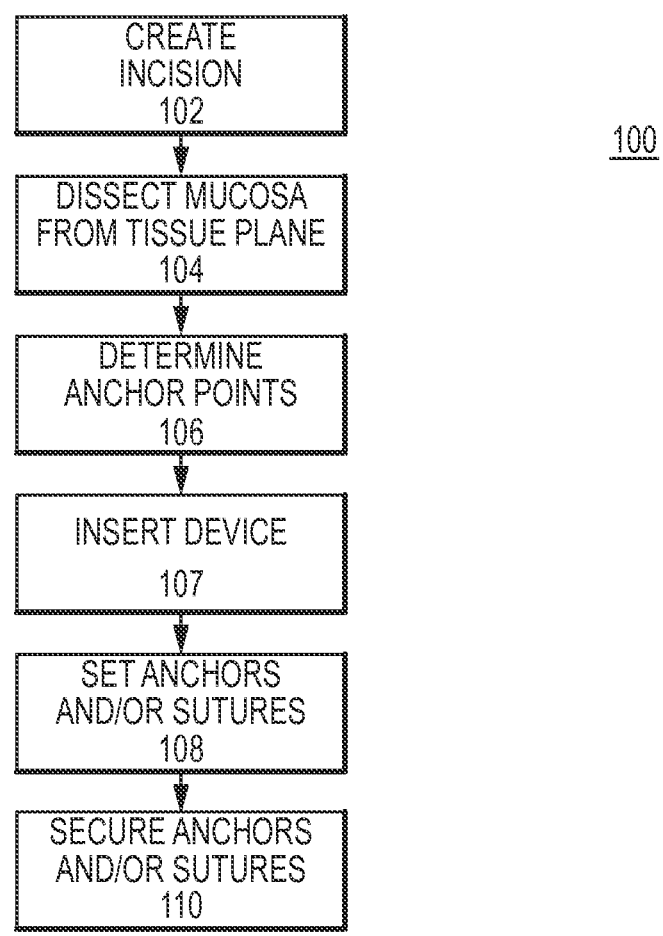
FIG. 1 illustrates a flow diagram highlighting aspects of a method according to an embodiment of the invention.

An embodiment of the invention is directed towards a medical device that can be used in areas of limited space and limited or no visualizabilitability, e.g., transvaginal pelvic surgery, repair of pelvic organ prolapse. In one embodiment, the medical device is configured for placement or passage of medical patches, sutures, stitches, tags including RFID tags, stereotactic tags, anchors, locating devices, sensors including chemical sensors, temperature sensors, and pressure sensors. The sensors may communicate wirelessly with external devices over a network. In one embodiment, the sensors use Bluetooth protocol for communication.

In one embodiment, the medical device is a configured to be used with one or more fingers, e.g., a finger-tip device, to place sutures, stitches, anchors, or tags, thereby allowing safe placement into any areas of the body that are difficult to reach or see. The device may be used for the placement of stereotactic markers into tissue near joints or tumors for guidance during orthopedic or neurosurgical procedures.

One embodiment includes a method and system for placement of sutures, stitches, anchors, sensors, or tags from a finger-tip device, allowing safe placement into any areas of the body that are difficult to reach or see. In one embodiment, the device includes a flexible tubular member having a lumen extending from a proximal end to a distal end. An actuator is configured to fit within a portion of the lumen and a finger sheath is coupled to a distal portion of a tubular member. An operating unit is releasably coupled to a distal end of the tubular member.

The operating unit is configured to operate with movement of the actuator from a first position to a second position. The operating unit is configured for placement of medical patches, sutures, anchors, locating devices, and sensors. In one embodiment, the assembly includes a sheath unit configured to receive at least one finger. In a preferred embodiment, the sheath unit is configured to receive at least two fingers. The sheath unit is configured to receive an operating unit and the operating unit is configured for placement or passage of medical patches, sutures, stitches, tags including RFID tags, stereotactic tags, anchors, locating devices, sensors including chemical sensors, temperature sensors, and pressure sensors.

In one embodiment, similar to neurosurgical stereotactic marker placement, placement of thermal sensors for cryotherapy and hyperthermia treatments, tissue sensors for biochemical markers like glucose, nitric oxide and oxygen that would be useful in diabetes, critical care and organ transplant management may be done.

One embodiment is directed towards a medical apparatus. The medical apparatus includes a tubular member having a lumen extending from a proximal end to a distal end, a finger assembly releasably coupled to a distal portion of the tubular member and an operating unit coupled to a distal end of the tubular member. The finger assembly includes a first finger slot and second finger slot.

Another embodiment is directed towards a medical device repairing an anatomical region with a device. The device includes a tubular member having a lumen extending from a proximal end to a distal end, a finger sheath unit coupled to a distal portion of the tubular member, an anchor unit releasably coupled to end of the tubular member configured to deliver an anchor and a flexible member coupled to the anchor unit. The finger sheath unit includes a first finger sheath and a second finger sheath arranged substantially in a similar plane. The flexible member includes a lumen extending from a proximal end to a distal end and is configured to receive an actuator. The actuator is configured to fit within a portion of the lumen of the flexible member and actuate the anchor unit upon movement of the actuator from a first location to second location.

One embodiment is directed towards a medical device for repairing female pelvic organ or tissue prolapsed region. The device includes a tubular member having a lumen extending from a proximal end to a distal end, a finger assembly releasably coupled to a distal portion of the tubular member, an operational unit releasably coupled to a distal region of the tubular member, and a flexible member coupled to the operational unit. The flexible member includes a lumen extending from a proximal end to a distal end and configured to receive an actuator. The operational unit is configured to deliver one of a suture or anchor to repair the prolapsed region upon actuation of the actuator. At least a portion of the actuator is configured to fit within a portion of the lumen of the flexible member and actuate the operational unit upon movement of the actuator from a first location to second location. The distal end of the flexible member is configured to extend outside a patient while the medical device is in use. The finger assembly includes a first open ended finger sheath and a second closed ended finger sheath arranged in a substantially similar plane.

One embodiment is directed to a method of repairing an anatomical region with an apparatus. The method includes creating an incision, developing access from the incision to the anatomical region, mapping of the anatomical region, inserting the device through the incision to the anatomical region and activating the device to deliver one of an anchor, suture, sensor, marker, and tag into the anatomical region.

Another embodiment is directed towards a method of repairing a prolapsed organ. The method includes creating an incision in an anterior vaginal mucosa, dissecting the mucosa from an underlying connective tissue, mapping a pelvic region of a patient, inserting a device through the vaginal incision into the pelvic region of the patient, and inserting at least one of an anchor and a suture into the pelvic region of the patient by actuating the device.

In embodiments, the mapping may be conducted with a visualization instrument or through tacitle feedback with or without the device. In preferred embodiment, the mapping is conducted with the device.

In one embodiment, the operating unit and sheath are configured to be releasably attached to each other. For example, a male and female connector may be used, tongue and groove connection, snap and groove connection, combinations of the same and the like. In a preferred embodiment, a connection mechanism is formed on the operating and includes a tapered ridge. The finger sheath includes a groove and receiver configured to be releasably coupled to the tapered ridge of the connection mechanism. It is noted that the connection mechanism may be configured on the finger sheath the groove and receiver may be configured on the operating unit and vice versa. Also, the finger sheath and operating unit may be one integral unit.

For example, the operating unit is described herein or may include an operating unit as described with reference to U.S. Pat. Nos. 4,726,371; 4,892,520; 5,079,629; 5,478,344; 5,538,506; 5,925,064; 6,048,351; 6,332,888; 6,475,135; 7,338,502 and U.S. Patent Application Publication Nos. 2004/0231167; 2008/0167680; 2010/0217282; 2011/0092985; and 2011/0092991, each of which are incorporated herein by reference in their entirety. The operating unit may be coupled to a flexible shaft or cable. The operating unit may be operated with a push button at the end of a flexible cable or alternatively operated with a thumb at the same end of the operating unit. The device is configured to allow a user to traverse a tortuous anatomy and also configured to have a mechanism to operate the operating unit at the same end as the operating unit or an end opposite to the operating unit and external to the patient.

In one embodiment, an exemplary use for the device is for the repair of female pelvic organ prolapse. A vaginal approach is preferred, but is difficult because of limited space and visualization. In this situation, and other surgical circumstances, the anatomical locations are easily accessible to fingertips, but less accessible using currently available unwieldy and rigid instruments. The device of this invention may allow access for the surgeons' fingers to be used to place a suture, anchor, tag, or sensor directly into the desired position by way of the vaginal approach and through small incisions and would allow the surgeon to map the surgical area. The instrument would allow precise placement of suture and/or anchors, which, may be used with autologous tissues or graft materials.

Biocompatible surgical mesh and medical patches may be attached to various portions of a body with the device, e.g., with anchors, sutures, staples out an operating unit of the device. In one embodiment, the biocompatible surgical mesh and patch materials may include patches and may be made from materials including but not limited to polymers, thermoplastics, and PTFE and biological materials. In addition, the materials may be bioabaorbable, resorbable, or permanent. Bioabsorbable materials include bioabsorbable polymers and copolymers composed from varying amounts of one or more of the following monomer examples, glycolide, d,1-lactide, 1-lactide, d-lactide, p-dioxanone (1,4-dioxane-2-one), trimethylene carbonate (1,3-dioxane-2-one), ε-caprolactone, γ-butyrolactone, δ-valerolactone, 1,4-dioxepan-2-one, and 1,5-dioxepan-2-one. These meshes may have any geometric shape and/or reinforced matrix. Specific examples of surgical mesh and medical patches that may be used include, but are not limited to, Ethicon Physiomesh™; Ethicon Proceed™; Ethicon Prolene™; Ethicon Vicryl™; Ethicon Ultrapro; Ethicon FlexHD™; Ethicon Mersilene™;

Ethicon Gynecare Gynemesh™; Boston Scientific Repliform®; Boston Scientific Xenoform®; Boston Scientific Polyform®; Bard Ventrio™; Bard Avaulta®; Bard Pelvitex®; Bard Pelvicol®; Bard Pelvisoft®; American Medical System (AMS) InteXen™; AMS Apogee™; AMS Perigee™; AMS Elevate®; Gore Gore-Tex®; Cook Biotech SymphaSIS™; and SurgiSIS®.

The sutures, anchors, staples and other attachment mechanisms used with the device, that is, the operating unit of the device may be made from materials including, but not limited to, thermoplastic, polymers, polypropylene, monocryl, polyglactin, polytetrafluoroethylene (PTFE), nylon and other biocompatible materials. Examples of sutures that may be used include, but are not limited to, Ethicon Prolene™; Ethicon Monocryl™; Ethicon Vicryl; Ethicon PDS; Ethicon Pronova™; Ethicon Ethibond; Ethicon Ethilon; and Covidien Dexon™. In addition, the materials may be bioabaorbable, resorbable, or permanent. Bioabsorbable materials include bioabsorbable polymers and copolymers composed from varying amounts of one or more of the following monomer examples, glycolide, d,1-lactide, 1-lactide, d-lactide, p-dioxanone (1,4-dioxane-2-one), trimethylene carbonate (1,3-dioxane-2-one), ε-caprolactone, γ-butyrolactone, δ-valerolactone, 1,4-dioxepan-2-one, and 1,5-dioxepan-2-one.

Moreover, the mesh, patch, sutures, anchors, staples and/or other attachment and implantable components may include an imaging material, e.g., echogenic material, radio opaque material, and the like. The radio opaque compounds may include ionic and non-ionic compounds. More specifically, radiographic materials as described with reference to U.S. Pat. Nos. 5,746,998 and 7,790,141 may used in the construction of the mesh, patch, sutures, anchors, staples and/or other attachment and implantable components.

In addition, the mesh, patch, sutures, anchors, staples and/or other attachment and implantable components may include radio frequency identification system, and more particularly RFID transponder as known in the art.

Various components of the device may be constructed from various materials as known in the art. For example, the tubular member, catheter, cable, rod, finger sheath and/or operating unit may be constructed from materials, such as polyesters, polyurethanes, polyamides, polyolefins including polyethylene and polypropylene, and any copolymers thereof. Some more specific examples of suitable materials include, but are not limited to: nylon; polyester elastomer; polyether/block polyamide, such as PEBAX, Hytrel, and/or Arnitel; polyamid such as Grilamid; flouro-polymer such as Kynar; polyether ether ketone (PEEK); polyethylene (PE); polyurethane; polyolefin copolymer (POC); and tetrafluoroethylenes such as polytetrafluoroethylene (PTFE).

Reference will now be made in detail to an embodiment of the present invention, example of which is illustrated in the accompanying drawings.

FIG. 1 illustrates a flow diagram highlighting aspects of a method according to an embodiment of the invention.

Referring to FIG. 1, the method is generally depicted as reference 100. The method includes creating an incision 102 at a desired situs, e.g., anterior vaginal mucosa, posterior vaginal mucosa, or vaginal apex. It is noted that the device and method may be used at other locations and for other uses. For example, the device may be used for setting markers or tags in orthopedic and neurosurgical procedures where navigation systems are used to guide placement of implants and the like. The mucosa is dissected 104 sharply and/or bluntly away from the underlying connective tissue plane (endopelvic fascia). Deficiency or breakdown of this connective tissue layer is what allows the prolapse and bulging of the vaginal walls and underlying pelvic organs into the vagina to occur, i.e., the bladder from anteriorly (cystocele), the rectum from posteriorly (rectocele), the uterus or intestines from superiorly (uterine prolapse or enterocele), on the vaginal walls from laterally (paravaginal defect).

The connective tissue plane can be traced to the pelvic side wall where substantial ligamentous and fascial structures exist and serve as landmarks and anchor points 106. The mapping may be done while the device is being used by the user, e.g., with one or more finger tips. After a map of the surgical area is developed, the device on two or more finger(s) is inserted the device into the vagina 107. The device is arranged on a co-axial orientation to an axis of the arm and/or hand to aid in orientation. Anchors and sutures are generally set into the sacrospinous ligament, arcus tendentious, obturator fascia and coopers ligament 108. Following this plane through a small vaginal incision to the pelvic sidewall is a basic gynecologic surgical maneuver. Once this plane is developed for the patient, the anatomical landmarks are easily palpable and the sacrospinous ligament, arcus tendineous, Cooper's ligament and obturator fascia are easily identified though very difficult to visualize.

The device may be used with surgeons' second and third fingers to aid in location and placement to a desired location on the pelvic wall and these fingers provide tactile feedback via an exposed fingertip. Moreover, as the sheath utilizes at least two fingers the orientation the stability of the device is readily maintained, e.g., middle finger and the ring finger; index finger and middle finger; or little finger and the ring finger. In this preferred embodiment, the user aligns the devices via their fingers, hand, and/or arm to ensure proper placement without sight. The device is not offset from fingers, hand, and/or arm, e.g., along a central axis, thereby allowing alignment even though there is no visualization.

Next, an anchor, with attached suture, is delivered from the device exactly to the desired location by pushing the button at the opposite end of the device. In a preferred embodiment, this is done while the surgeon is still in contact with the pelvic wall. With the anchor exposed, and pressure delivered 110 at the closed finger-tip end, the device will set the anchor into the tissue at the desired location in the pelvic wall. In a preferred embodiment, the anchor and mesh are configured to repair, secure, or reattach the underlying connective tissue, or anchor graft material that substantially supports the prolapsed organs.

Optionally, sutures may be attached to these anchors and can be used to support the vaginal wall itself, with or without the use of a graft. With the safety of vaginal mesh under scrutiny by the FDA, many surgeons are returning to use mesh-free repairs. The device described herein would make those procedures much easier.

Alternatively, anchors and sutures in the sacrospinous ligament, arcus tendentious, obturator fascia and/or coopers ligament could also be used to suture graft material over the deficient connective tissue plane for a graft augmented repair. Alternatively, anchors without sutures may be used to directly tack graft material to the desired location.

In still other embodiments, the operating unit of the device may be modified with devices known in the art. For example, the operating unit may include a scope to give active visual aid to the surgeon. In another example, the operating unit of device may include a endoscopic suture device or anchor device configured to secure the graph or support an prolapsed area. By way of example, the endoscopic suture systems may be incorporated in the operating unit and include systems as known in the art, e.g., as disclosed in U.S. Pat. Nos. 5,364,408; 5,458,609; 5,478,344; 5,540,704; 5,575,800; 5,578,044; 5,662,664; 5,700,272; 5,713,910; 5,741,277; 5,741,279; 6,048,351; 7,582,096, and U.S. Patent Application Publication Nos. 2010/0217282; 2011/0092985 and 2011/0092991, all of which are herein incorporated by reference.

The suture device may be used in laparoscopic procedures. The suture device, and in particular the head of the device, may be used with the present invention by attaching the head of the suture device to the finger sheaths of the present invention. In general, the suture device automatically throws, catches and retrieves a suture through the head of the device. An example of a suture device is described in U.S. Pat. Nos. 5,741,277 and 7,582,096, which are incorporated herein by reference.

Figure 2:
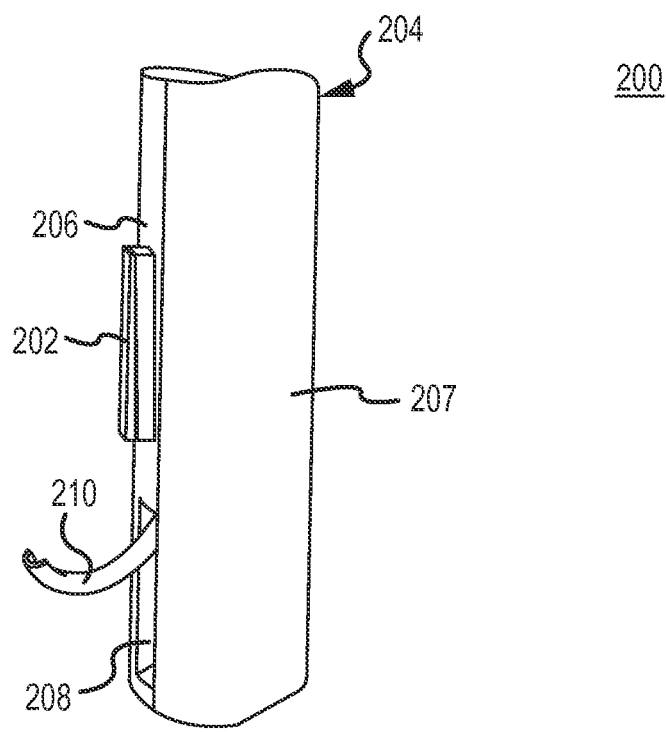
FIG. 2 illustrates a perspective view of an endoscopic suture device according to an embodiment of the invention.

FIG. 2 illustrates a perspective view of an endoscopic suture device according to an embodiment of the invention.

Referring to FIG. 2, an apparatus is generally depicted as reference number 200. The apparatus 200 includes a connection mechanism 202 fixed to an end portion of the tubular member 204. A finger sheath (not shown), described with reference to FIGS. 7A-15 is utilized with this device 200 and configured to be coupled to the device 200 via the connection mechanism 202 as described with reference to FIGS. 13-15.

The apparatus 200 includes the body 204 having a first half 206 and a second half 207. A needle slot 208 is utilized to deploy a cannula 210 out of the cannula body 204. The cannula 210 can be utilized with other instruments as known in the art. For example, the cannula 210 is utilized to deploy a needle and sutures (not shown). Alternatively, other secondary devices may be delivered through the cannula 210, e.g., visualization devices.

Figure 3:
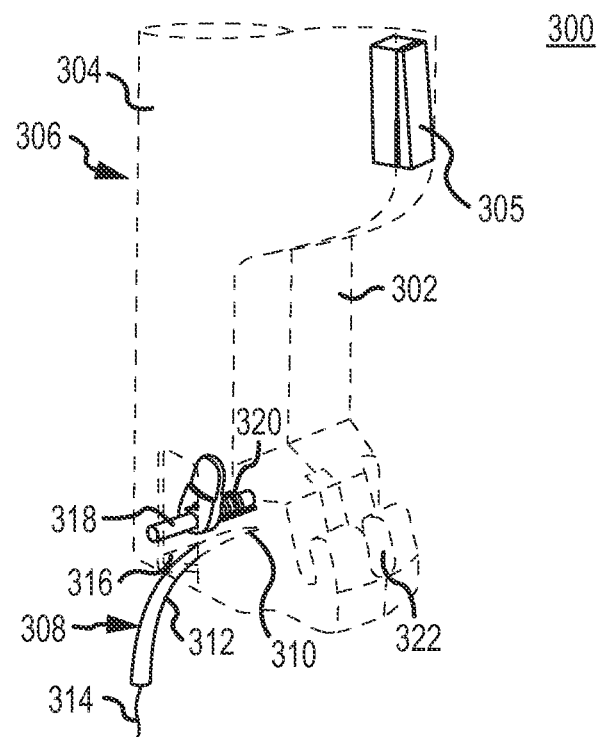
FIG. 3 illustrates a perspective view of a needle catch mechanism with a needle and a phantom view of a cannula body according to another embodiment of the invention.

FIG. 3 illustrates a perspective view of a needle catch mechanism with a needle and a phantom view of a cannula body according to another embodiment of the invention Referring to FIG. 3, the suture system is generally depicted as reference number 300. The suture system includes a first half 302 and a second half 304 configured to form a body 306. The system 300 includes a connection mechanism 305 fixed to an end portion of the tubular member 306. A finger sheath (not shown), described with reference to FIGS. 7A-15 is utilized with this device 300 and configured to be coupled to the device 300 via the connection mechanism 305 as described with reference to FIGS. 13-15.

A surgical needle 308 includes a needle tip 310 and a needle body 312, and a suture 314. A retainer lever 316 is pivotally mounted on a shaft 318 and is biased to a neutral position by a spring 320 or other suitable mechanism. A needle guide track terminates in an exit opening 322. A flexible needle driver guide track and the needle guide track combine to form a continuous pathway in which a flexible needle driver with a needle driver tip is slidably disposed. The needle 308 is inserted through the exit opening 322. The needle 312 and the suture 314 are inserted into the needle guide track until the needle tip 310 is positioned adjacent to the exit opening 322. It may be seen that during insertion into the needle guide track, the needle 308 causes the retainer lever 316 to rotate pivotally on the shaft 318 to a retracted position. In operation, an actuator (not shown) is operated to advance the needle 308.

To retrieve the needle 308 and the suture 314 the cannula body 306 is placed in the surgical field and maneuvered to guide the needle tip 310 and needle shaft through an opening in a needle catch, which includes the opening and a catch bottom. The flexible needle driver is advanced in the needle guide track, engaging and pivotally rotating the retainer lever 316 and pinching and capturing the needle body 312 between the retainer lever 316 and a catch bottom. The needle 308 and the suture 314 may then be removed from the surgical field through the surgical trocar or other suitable instrument. To release the needle 308 from being pinched by the retainer lever 316 and the catch bottom, the flexible needle driver is retracted, allowing the retainer lever 316 to return to the neutral position, thus freeing the needle 308.

In still other embodiments, an apparatus such as a suture device may be modified with aspects of the invention including a finger sheath and connection mechanism to provide a device that allows for advantages of the invention. Examples of devices that may be modified are disclosed in U.S. Pat. Nos. 7,828,189; 7,828,798; and 7,789,878; and U.S Publication Nos. 2010/0094083; 2010/0217282; 2010/0274265; 2011/0040308; 2010/0147921; 2006/0036232; 2009/0248046; and 2009/0259233, and are each incorporated by reference, in particular, the portions of the disclosures describing the head of the endoscopic stitching device. More specifically, each of the foregoing may be modified and adapted for use with a connection mechanism 305 fixed to an end portion of any of the foregoing devices. A finger sheath (not shown), described with reference to FIGS. 7A-15 is utilized with this any of the foregoing modified devices and configured to be coupled to the device via the connection mechanism 305 as described with reference to FIGS. 13-15.

Figure 4:
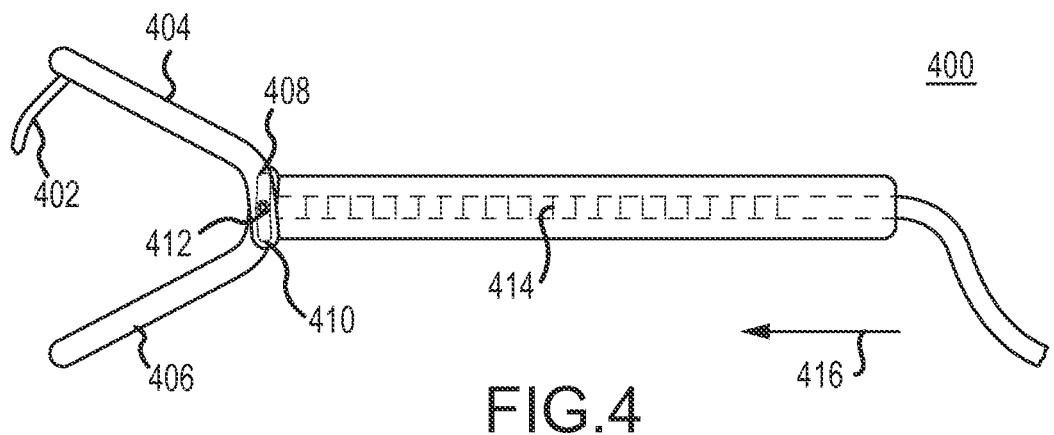
FIG. 4 illustrates a cross-section view of a stitching device in an open condition according to another embodiment of the invention.
Figure 5:
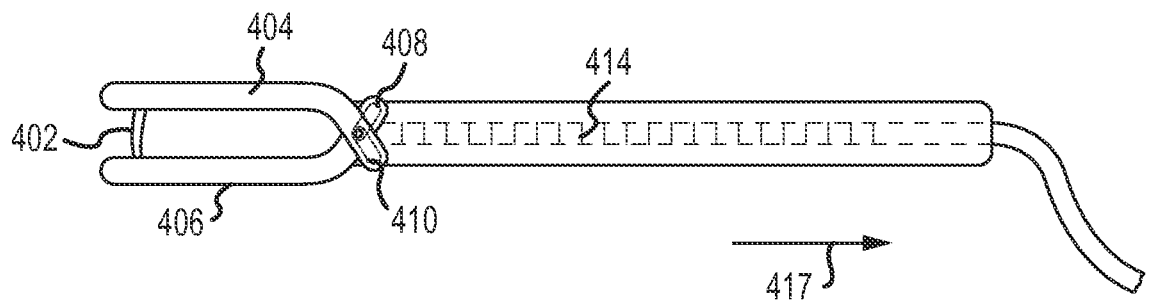
FIG. 5 illustrates a cross-section view of the stitching device of FIG. 4 in a closed condition.
Figure 6:
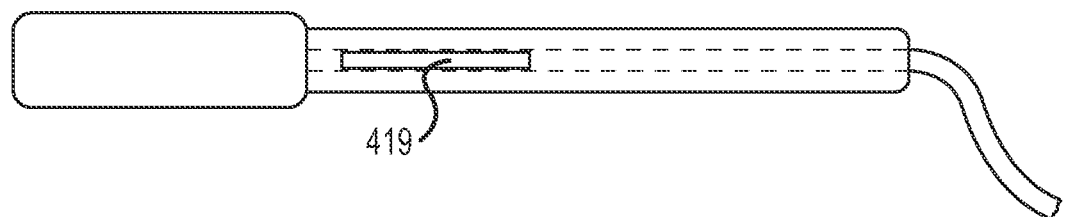
FIG. 6 illustrates a bottom of the stitching device of FIG. 4.

FIG. 4 illustrates a cross-section view of a stitching device in an open condition according to another embodiment of the invention. FIG. 5 illustrates a cross-section view of the stitching device of FIG. 4 in a closed condition. FIG. 6 illustrates a bottom of the stitching device of FIG. 4.

Referring to FIGS. 4-6, a suture system 400 includes a needle 402 coupled to a first end 404, the needle is configured to be received by a second end 406. A recess is formed in the second end 406 to receive a portion of the needle 402. The first end 404 and second end 406 are maintained in an open position by an actuating mechanism. The actuating mechanism includes a first slot 408 in the first end 404, a second slot 410 on the second end 406, and a pin 412 is in communication with the first slot 408 and second slot 410. The pin 412 is coupled to an actuator 414, e.g., cable, rod and the like, configured to move the pin from a first position to a second position as indicated by arrow 416, thereby moving the first end 404 and second end 406 from a closed position to an open position and vice versa.

Referring to FIG. 5, the suture system 400 is in a closed position. The closed position is achieved by moving the actuator 414 from a first position to a second position as indicated by arrow 417 to open the device. When the device is closed, the needle 402 is moved into of the recess of the second end 406. If tissue were present between the first and second end 404, 406, the needle 402 would penetrate through the tissue prior to the entrance into recess.

FIG. 6 shows a bottom view of the suture system 400. The bottom portion includes a connection mechanism 419. A finger sheath (not shown), described with reference to FIGS. 7A-15 is utilized with this device 400 and configured to be coupled to the device 400 via the connection mechanism 419 as described with reference to FIGS. 13-15.

Figure 7A:
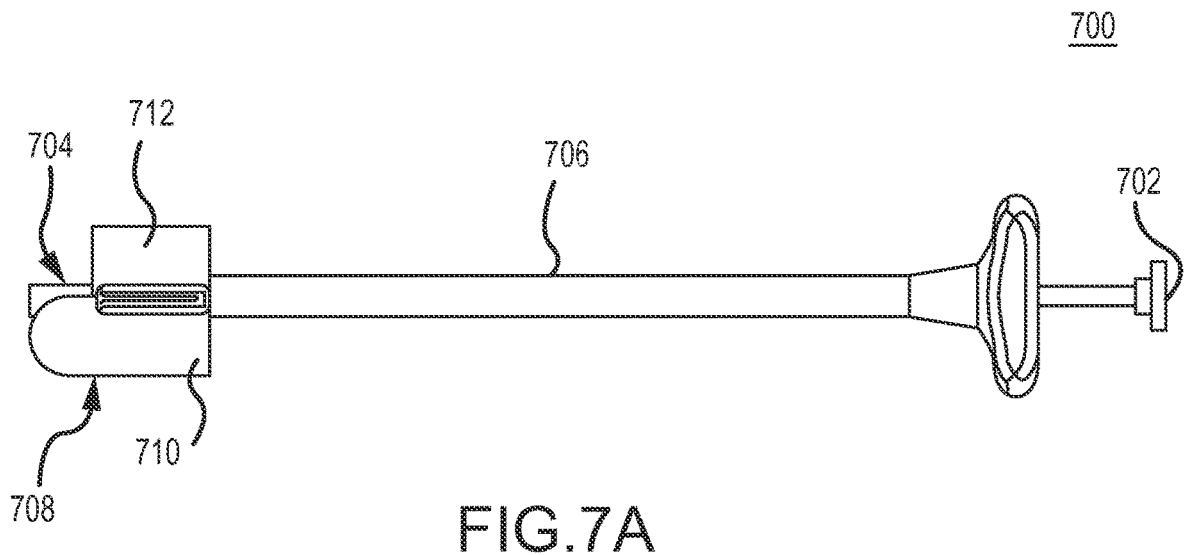
FIG. 7A illustrates a top view of a device according to another embodiment of the invention.

FIG. 7A illustrates a top view of a device according to another embodiment of the invention.

Referring to FIGS. 7A, the assembly is generally depicted as reference number 700. The assembly 700 includes an actuator 702 configured to actuate the delivery of an anchor from a unit 704 at the opposite end of the device 700. The unit 704 is coupled to the flexible shaft 706 and both are constructed from materials known in the art, e.g., thermoplastic material. The shaft 706 may be any length, e.g., equal to, greater than or less than the length of a finger sheath unit 708. An anchor (not shown) is delivered from the unit 704 at a distal end of the instrument when the actuator 702 is actuated. Furthermore, the user may insert additional anchors into a portion of the shaft 706 during use by removing the actuator 702, inserting an anchor and reinserting the actuator 702. In addition, additional anchors may be added to the unit 704 during or before use, e.g., another unit 704 can be removed and recoupled to the shaft 706 as a cartridge attachment or the unit 704 may be refilled. The actuator 702 may be a plunger or other actuator mechanism 702 configured to deliver an anchor from the unit 704. For example, the actuator may be a cable, remote control, spring driven, hydraulic or other pressure driven mechanism, or combinations of the same and the like.

The finger sheath unit 708 is removably coupled to the shaft 706 and includes at least two finger slots 710 and 712 configured to receive at least a portion of user's fingers. It is noted that finger slots 710 and 712 may include a supplemental medical devices rather than a finger slot or in addition to a finger slot, e.g., a cutter, visualization aids, storage, laser ablation devices and the like, may be coupled to at least one of the finger slots 710, 712 or as an additional feature adjacent to one of the finger slots 710, 712. A visualization aid may include radio opaque (RO) markers, camera with or without light, or other visualizations aids as known in the art. The finger slots 710 and 712 are oriented to be co-axial and/or in substantially the same plane with the unit 704 and/or centered over the unit 704. The co-axial, same plane and/or centered orientation enables a user to align the unit 704 without the need for visualization or with poor visualization. In one embodiment, one of the at least two finger slots is not a finger slot, but rather a supplemental treatment device or visualization aid. Moreover, the two finger slots may include one finger slot, two finger slots or three finger slots.

In use, the apparatus 700 is guided to the desired treatment situs with a user's fingers in the finger sheaths 710 and 712 to a treatment situs. In this embodiment, the finger sheath 712 is an open end finger sheath and the finger sheath 710 is a closed end finger sheath. The open end of finger sheath 712 allows for accurate tactile feedback with a user's finger. The closed end of the finger sheath 708 allows for additional pressure and stability to be exerted on an anchor during insertion and when it is in place. It is noted that each of the finger sheaths may be adjustable to receive a plurality of different finger sizes, e.g., the diameter of the finger sheath may be adjustable with a ratchet or other mechanism. Moreover, the finger sheath may be configured to cover only a quarter or less of an end portion of predetermined finger of a predetermined user.

It is also noted that the finger sheath 710 and finger sheath 712 may be arranged in different planes with respect to each other. That is, the first finger sheath 710 and second finger sheath 712 may be arranged at any angle from 0 to 360 degrees around the shaft 706. Moreover, the finger sheaths may be arranged at an angle from the shaft, e.g., about 1 degree to about 20 degrees or greater. The first finger sheath 710 may have a portion, e.g., the distal end, located proximally from the second finger sheath 712. In still other embodiments, three finger sheaths may used. In this embodiment, the finger sheath 710 and finger sheath 712 are arranged in substantially the same plane with respect to each other.

Figure 7B:
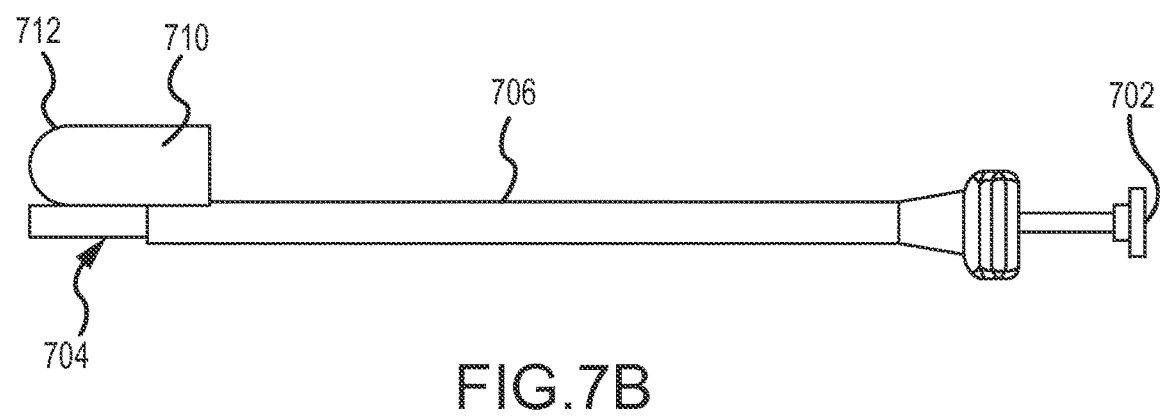
FIG. 7B illustrates a side view of the device in FIG. 7A.

FIG. 7B illustrates a side view of the device in FIG. 7A.

Figure 9:
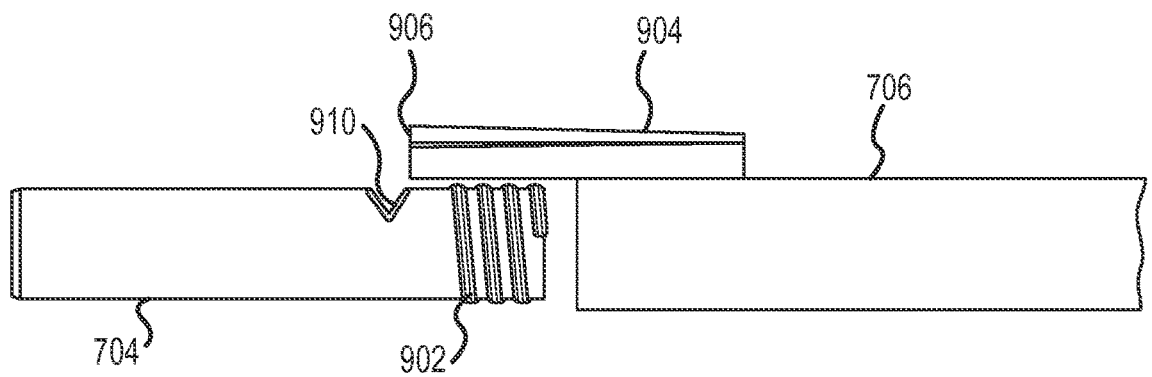
FIG. 9 illustrates a magnified view of a cylinder portion of the device in FIG. 7A or FIG. 8.

Referring to FIG. 7B, the finger assembly unit 708 includes finger sheaths 710 and 712. The finger assembly unit 708 is coupled to the shaft 706 (as will be seen in FIGS. 13-14). The unit 704 is also coupled to the shaft 706 (as shown in FIG. 9). The unit 704 is configured to deliver an anchor to a treatment situs upon actuation of the actuator 702.

In this preferred embodiment, the distal end of the unit 704 is terminated at about the same distance as the closed end of the finger sheath 710. This termination distance allows for leverage in placing a suture, anchor or other item, assists in increasing the effect of the force exerted on the device 700, and permits precise location when visualization is not available or poor. Of course, the distal end of the unit 704 may be located at a distance proximal or distal to either of the finger sheaths 710, 712.

In another embodiment, the actuator 702 may be placed directly adjacent the unit 704 and there is no tubular member 706 (not shown). This compact configuration is actuated by a user with the same hand as in the finger sheath 708 rather than a different hand.

Figure 8:
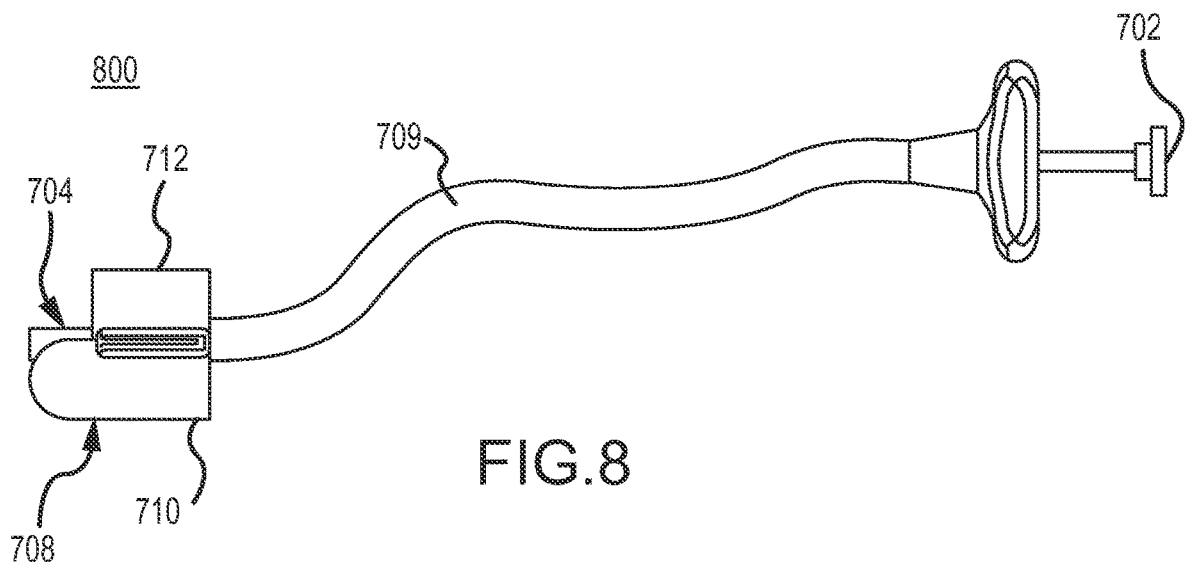
FIG. 8 illustrates a top view of a device according to another embodiment of the invention.

FIG. 8 illustrates a top view of a device according to another embodiment of the invention.

Referring to FIG. 8, the apparatus 800 includes a unit 704 configured to deliver anchors coupled to a flexible cable 709. The flexible cable 709 permits access to a tortuous anatomy. Moreover, a distal end portion of the cable 709 may include a flexible shaft.

FIG. 9 illustrates a magnified view of a cylinder portion of the device in FIG. 7A of FIG. 8.

Referring to FIG. 9, the unit 704 is coupled to the shaft 706 or cable 709. The unit 704 is configured to deliver anchors to a treatment situs and includes a window 910. The window 910 is configured as an oval-shaped opening or other geometric shape in the wall of the unit 704. A suture (not shown) can be attached to the anchor (not shown) via this opening 910. The suture can extend out the window 910. In this embodiment, the unit 704—is coupled to the shaft 706 or cable 709—with threads 902 that allow it to be securely coupled. The unit 704 may be connected to the shaft 706 prior to connecting the finger assembly 708 or following the attachment of the finger assembly 708.

Other connection mechanisms other than threads 902 may be used to couple the unit 704 to the shaft 706 or cable 709, e.g., a pressure fit coupler, adhesive, releasable engagement device and the like. Furthermore, the connection may be permanent or it may be temporary.

A connection mechanism 904 is fixed to, and extends past, the upper side of the shaft 704. The connection mechanism 904 is configured to accept a finger assembly 708 (not shown) by sliding the assembly 708 into position via the tapered ridge 906. Another type of coupler may be utilized to attach the finger sheath 708 to the shaft 706, e.g., the finger sheath 708 may be permanently attached to the shaft 706 by adhesive, chemical bonding, welding, or other technique. Moreover, the finger assembly 708 and shaft 706 may be formed as a one-piece unit.

Figure 10:
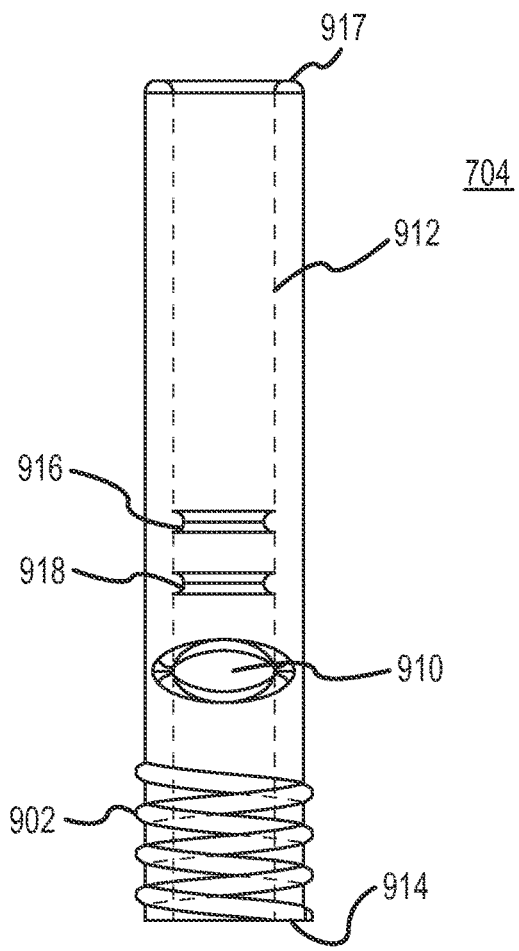
FIG. 10 illustrates a detailed view of the cylinder portion in FIG. 9 without an anchor.

FIG. 10 illustrates a detailed view of the cylinder portion in FIG. 9 without an anchor.

Referring to FIG. 10, the unit 704 includes cylinder threads 902 on a proximal portion of the unit 704. The unit 704 includes a lumen 912 extending from a distal end 914 to a proximal end 917. Near a middle portion of the lumen 912 are two internal ribs, a first rib 916 and a second rib 918. A base of an anchor (not shown) will be held in position between the ribs 916, 918. The opening 910 is configured to allow for a suture (not shown) attached to the anchor to exit the cylinder. Various types of anchors may be used with or without sutures could be used.

Figure 11A:
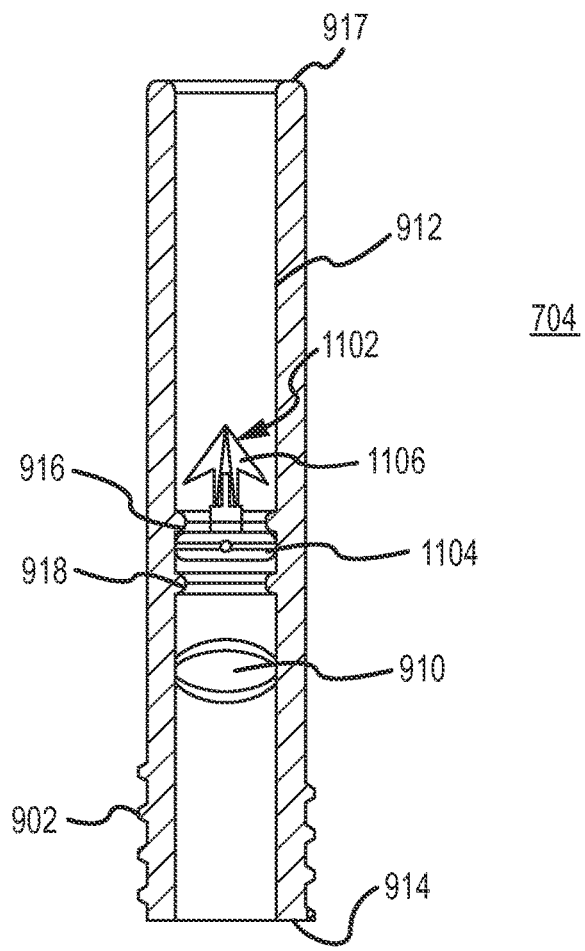
FIG. 11A illustrates a cross-sectional detailed view of the cylinder portion of FIG. 7A with an anchor.
Figure 11B:
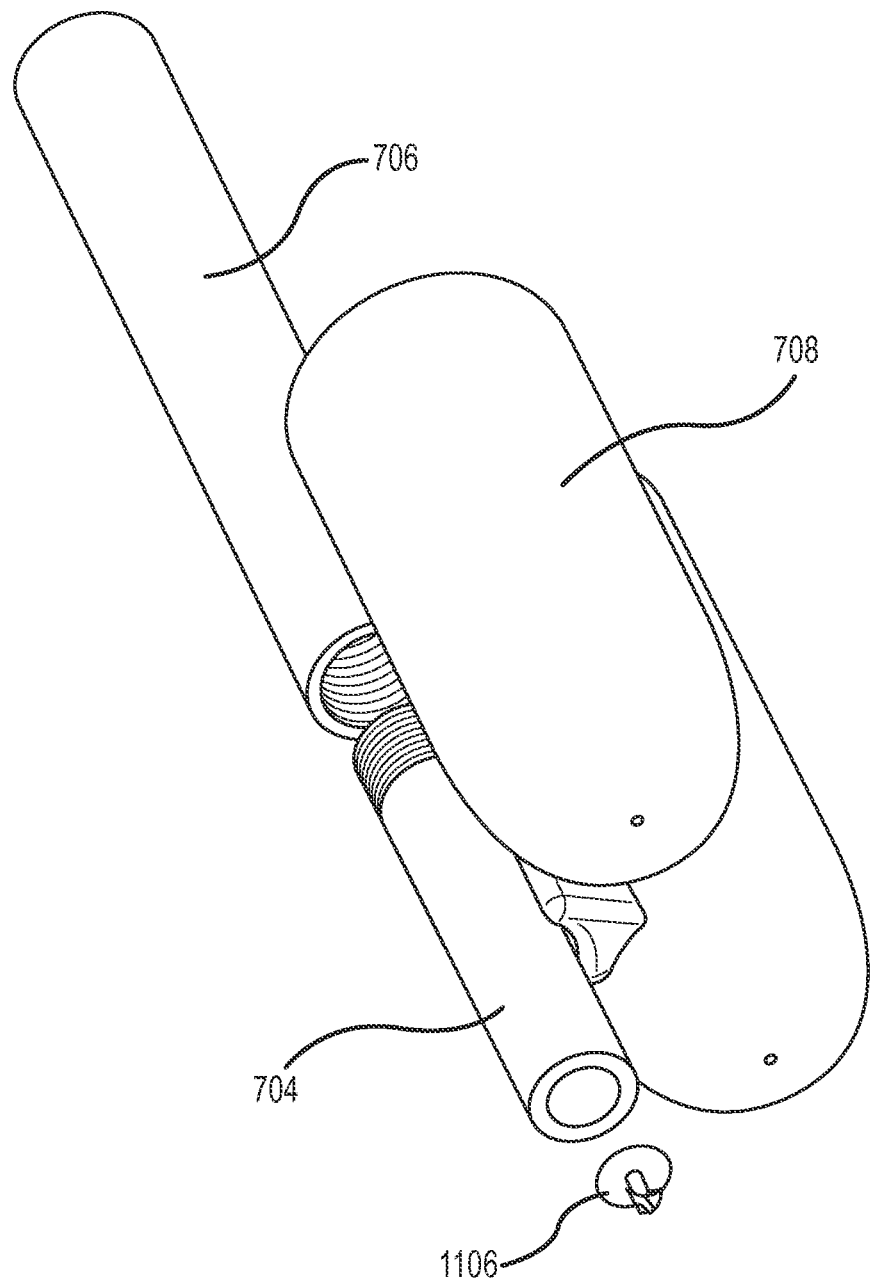
FIG. 11B illustrates a perspective view of a device according to an embodiment of the invention.

FIG. 11A illustrates a cross-sectional detailed view of the cylinder portion of FIG. 7A with an anchor. FIG. 11B illustrates a perspective view of the device in FIG. 11 with a finger assembly.

Referring to FIGS. 11A and 11B, the unit 704 includes an anchor 1102 having a base portion 1104 and tip portion 1106. The tip portion 1106 includes a barb type geometry configured to penetrate tissue and prevent removal. The anchor 1102 is held in position between the two internal ribs 916, 918. In a preferred embodiment, the anchor tip portion 1106 includes an arrow shaped barb. In use, the plunger or other actuator (not shown) contacts the base portion 1104 of the anchor 1102 and releases the anchor 1102 from the internal ribs 916, 918. The anchor 1102 passes down the lumen 912 and out a distal end 917 of the unit 704 to be placed in the desired situs of the patient. In operation, a tack 1106 exits a distal end of the unit 704 upon activation of the actuator. The tack 1106 could be used to secure graft material, other material to itself or other regions, and the tack can include radiopaque (RO) marker, RFID tag active or passive, sensor and other devices.

Figure 12:
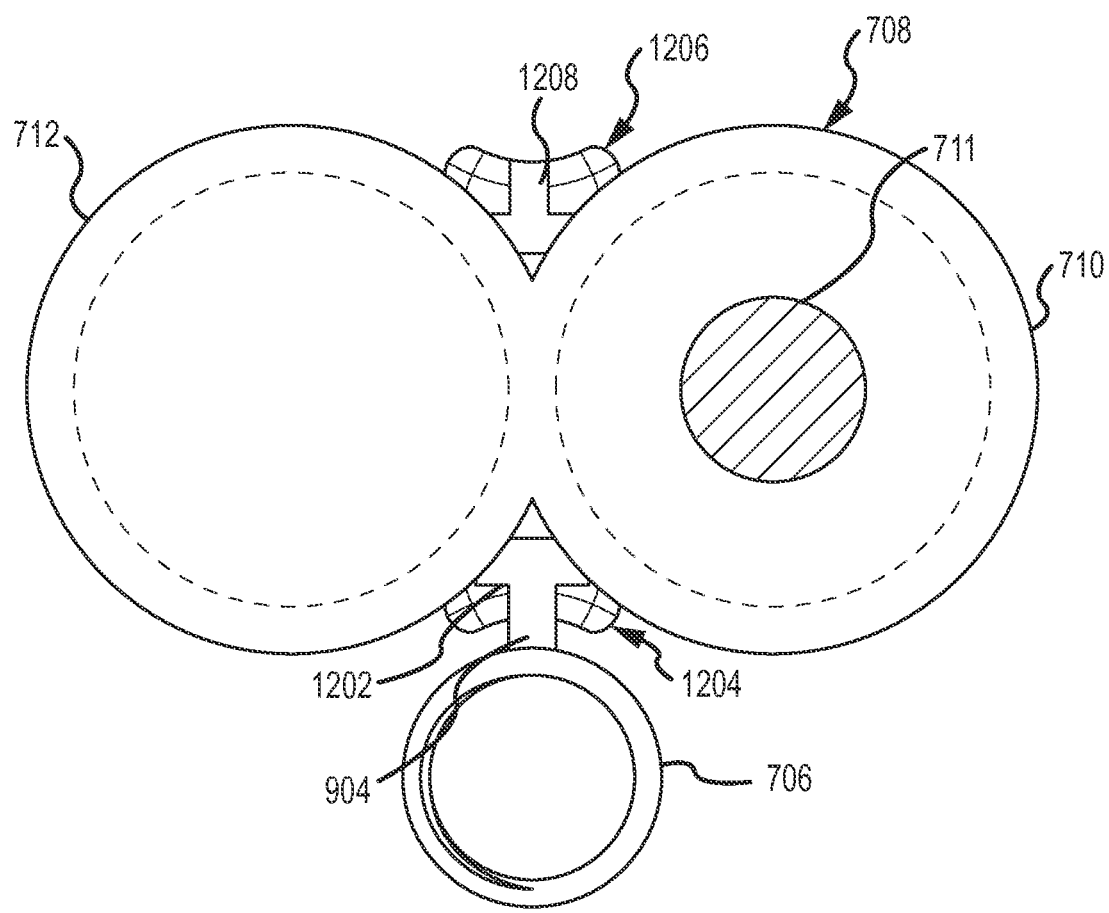
FIG. 12 illustrates an end view of FIG. 7A without a unit attached.

FIG. 12 illustrates an end view of FIG. 7A without a unit attached.

Referring to FIG. 12, an end portion of the finger sheath unit 708 is shown having a finger assembly 708 attached. The finger assembly 708 includes a first finger sheath 710 and a second finger sheath 712. Optionally, the first finger sheath 710 includes a hole 711 at end portion of the finger sheath 710. The hole 711 can be sized to allow for tactile feedback to the user's finger. The hole 711 may be of any geometric configuration, e.g., circular, oval, triangular, square, etc. In this configuration, the apparatus does not have a unit 704 attached to the shaft 706 or cable 709. The shaft 706 employs a tapered ridge 904 which slides into a groove 1202 on a receiver 1204 which is located between the finger sheaths 710, 712. The tapered ridge 904 of a connection mechanism 906 may be permanently or temporarily attached to the shaft 706. In some embodiments, the finger sheath 708 is permanently attached to the shaft 706.

Moreover, an additional receiver 1206 may be used on another side of the finger sheath 710, 712. In this embodiment, an additional receiver 1206 is coupled to an opposite side of the finger sheath unit 708. The additional receiver 1206 includes a T-shape opening 1208 configured to receive a tapered ridge 904, but may be any suitable geometric shape. The receiver 1206 is configured to receive a tapered ridge 904 of a connection mechanism 906. Furthermore, the receiver 1206 and opening 1208 are configured to lock once the tapered ridge 904 is in place to secure the finger sheath unit 708 to the shaft 706. As illustrated, the finger sheath 712 is open for the finger-tip to be exposed and allow tactile sensation for guiding the device onto position. The other finger sheath 710 is closed to allow finger tip pressure to push the anchor into the tissue. The additional receiver 1206 allows a user to switch the orientation of the finger sheaths 712, 710, e.g., from right to left orientation and vice versa. Moreover, any operating unit may be utilized with finger assembly including a suture unit, staple unit, visualization unit and sensor unit as described herein.

Figure 13:
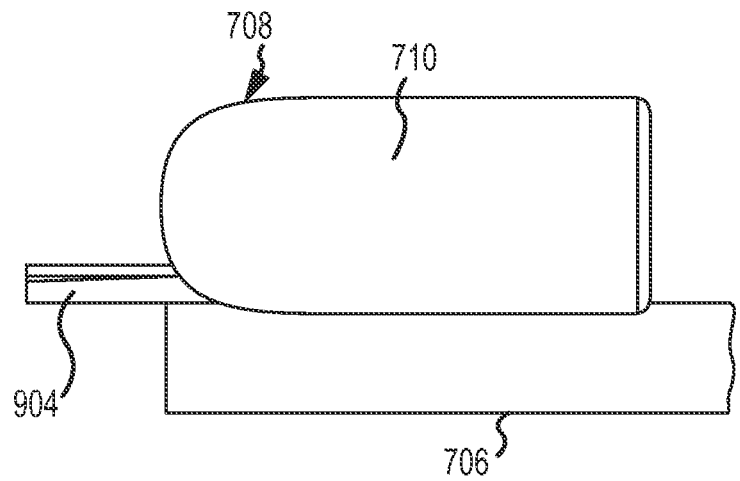
FIG. 13 illustrates a magnified view of a distal portion of the device in FIG. 7A or 8.
Figure 14:
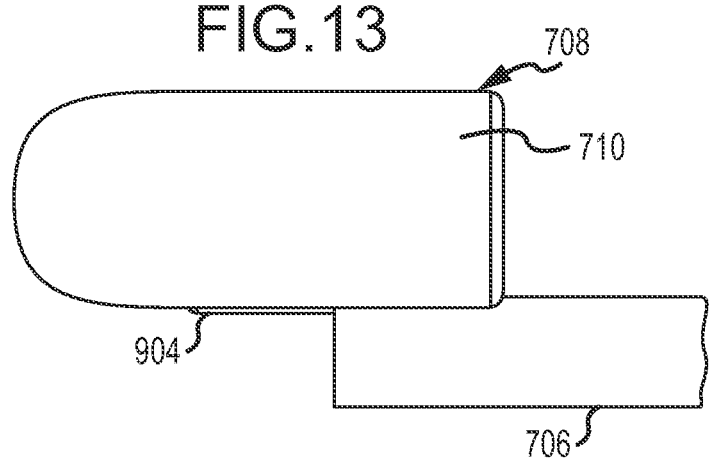
FIG. 14 illustrates a magnified view of a distal portion of the device in FIG. 13.
Figure 15:
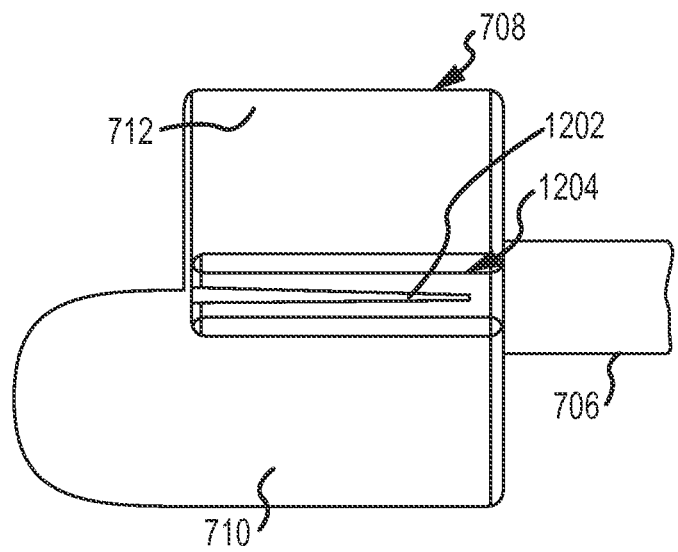
FIG. 15 illustrates a magnified view of a distal portion of the device in FIG. 7A or FIG. 8.

FIG. 13 illustrates a magnified view of a distal portion of the device in FIG. 7A or 8. FIG. 14 illustrates a magnified view of a distal portion of the device in FIG. 13. FIG. 15 illustrates a magnified view of a distal portion of the device in FIG. 7A or FIG. 8.

Referring to FIGS. 13-15, these figures represent attaching the operating unit 708 to a shaft 706. The finger sheath unit 708 includes a first finger sheath 710, second finger sheath 712, and a receiver 1204 including a tapered groove 1202. The groove 1202 and receiver 1204 are configured to be releasably coupled to the tapered ridge 904. The groove 1202 includes a locking portion to lock with a portion the ridge 904 (not shown). In operation the sheath unit 708 slides onto the ridge 904 of the shaft 706 or cable 709 as shown sequentially in FIGS. 13-15.

Figure 16:
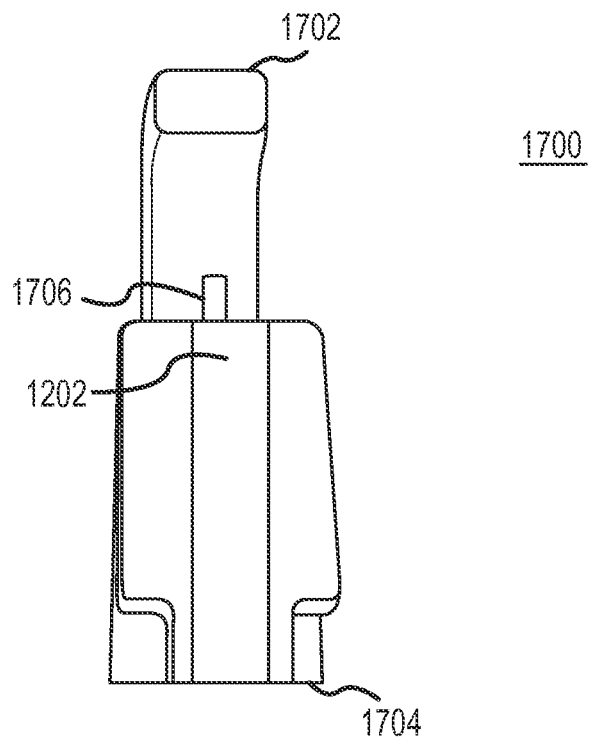
FIG. 16 illustrates a bottom view of a unit according to another embodiment of the invention.
Figure 17:
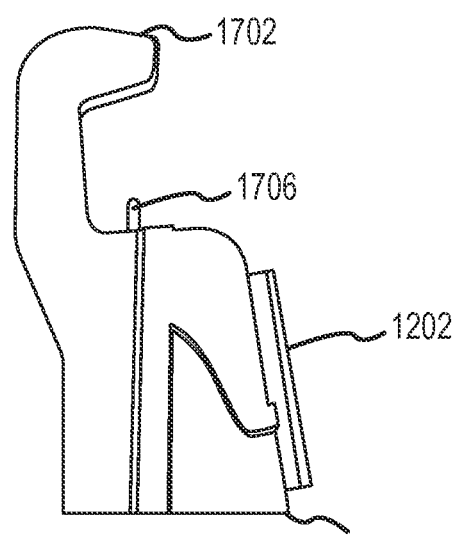
FIG. 17 illustrates a side-view of the device in FIG. 16.

FIG. 16 illustrates a bottom view of a unit according to another embodiment of the invention. FIG. 17 illustrates a side-view of the device in FIG. 16.

Referring to FIGS. 16-17, the device 1700 is configured to provide sutures to predetermined situs. The device 1700 includes a proximal end 1704, a distal end 1702, a tapered groove 1202, and a needle 1706. The tapered groove 1202 is configured to be releasably coupled to a receiver (not shown) as described herein. Moreover, a finger assembly is configured to be releasably coupled to the device 1700. The device 1700 is actuated with an actuator as described herein and known in the art. A finger sheath (not shown) of the finger assembly, but described with reference to FIGS. 7A-16 is utilized with this device 1700 and configured to be coupled to the device as described with reference to FIGS. 13-15.

Figure 18:
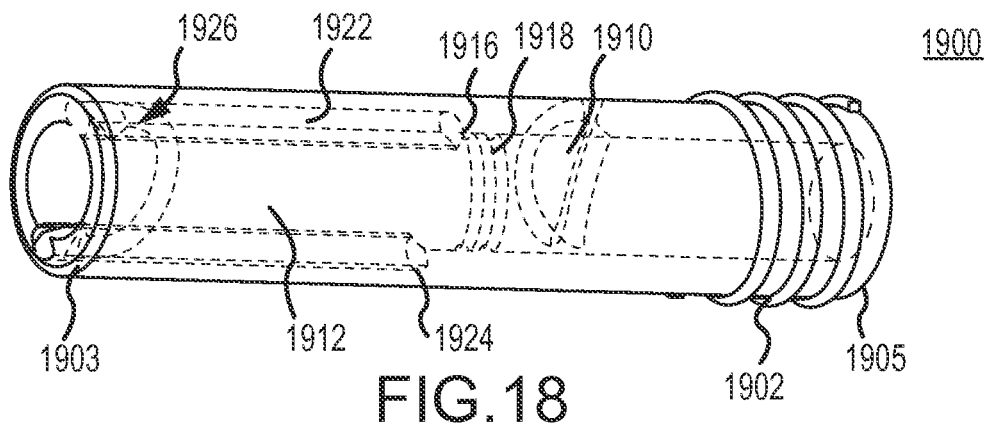
FIG. 18 illustrates a detailed view of a unit according to another embodiment.
Figure 19:
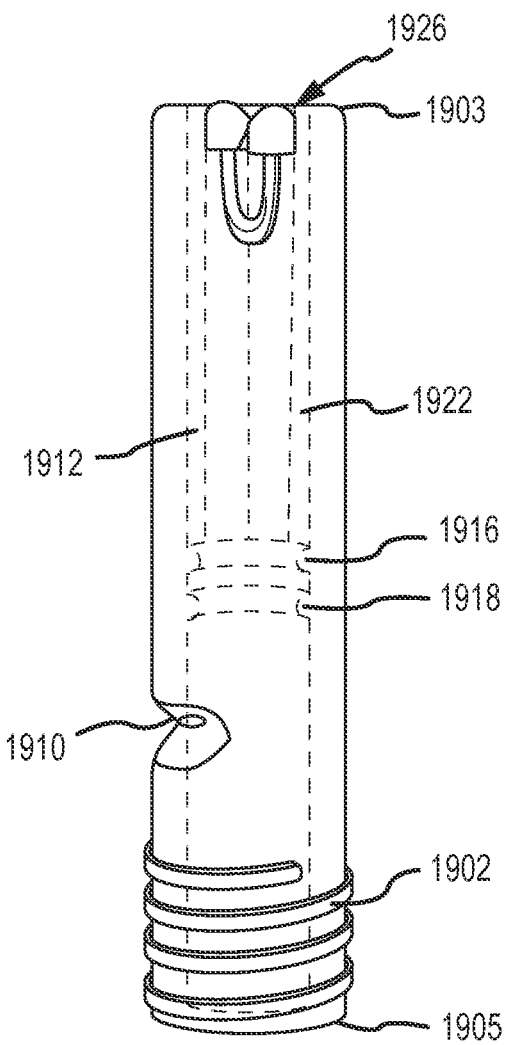
FIG. 19 illustrates a detailed view of FIG. 18 with an anchor.
Figure 20:
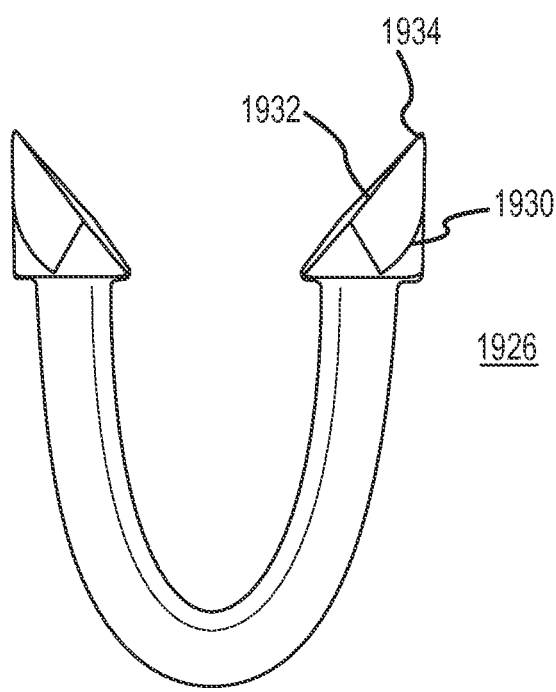
FIG. 20 illustrates an anchor according to another embodiment of the invention view.
Figure 21:
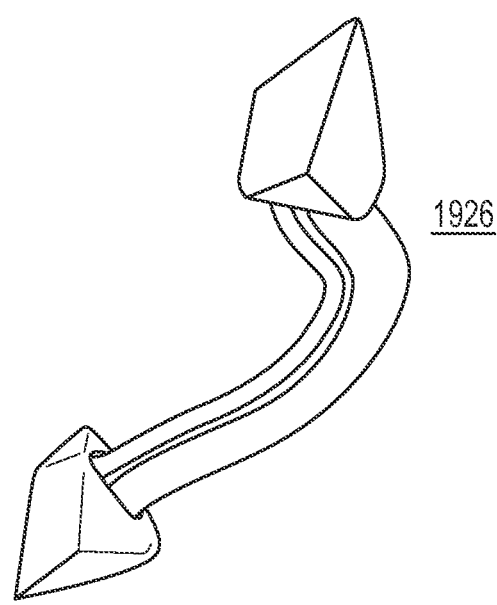
FIG. 21 illustrates an anchor of FIG. 20 in a second configuration.
Figure 22:
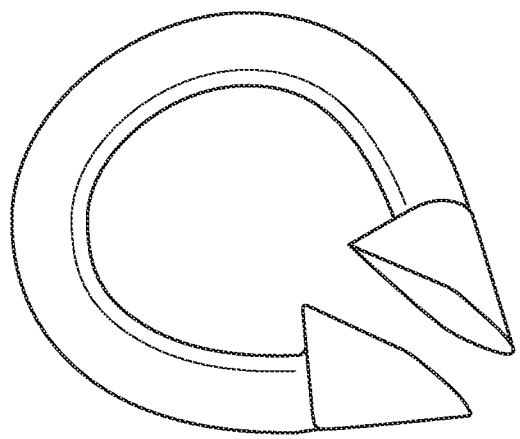
FIG. 22 illustrates an anchor of FIG. 21 in a third configuration.

FIG. 18 illustrates a detailed view of a unit according to another embodiment. FIG. 19 illustrates a detailed view of FIG. 18 with an anchor. FIG. 20 illustrates an anchor according to another embodiment of the invention view. FIG. 21 illustrates an anchor of FIG. 20 in a second configuration. FIG. 22 illustrates an anchor of FIG. 21 in a third configuration.

Referring to FIGS. 18-22, the actuator unit is generally depicted as reference number 1900. The unit 1900 includes threads 1902, a proximal end 1905, a distal end 1903 and a lumen 1912 extending from a proximal end 1905 to a distal end 1903. The lumen includes a first slot 1922, second slot 1924, a window 1910 and first internal ridge 1916 and second internal ridge 1918. An anchor 1926 is configured to slide with a first slot 1922 and second slot 1924.

The anchor may include a RFID tag, transponder and/or imaging material as described herein. In this embodiment, the anchor is constructed from an elastic material. The anchor 1926 is a compressed configuration within the first slot 1922 and second slot 1924 as shown in FIG. 20. After the anchor is released from the slot it expands to a second expanded position a deployed configuration as shown in FIG. 21. FIG. 22 illustrates the anchor in a staple like configuration. This deployed configuration will aid in the attachment to tissue. The anchor 1926 also includes a sharp tip 1934 of any geometry. In this embodiment, the anchor 1926 includes a sharp tip 1934 at a first angle, a first cutting surface 1932, and a second angle cutting surface 1930. Of course, other anchors of other geometric configurations may be used. The anchor may be configured with a plurality of cutting surfaces with or without sutures. The anchors may be made with material that when released returns to an expanded shape (FIG. 21). The anchors may be reinforced with an internal or external stiffening element, e.g., metal rib, wire or the like.

The inventions and methods described herein can be viewed as a whole, or as a number of separate inventions that can be used independently or mixed and matched as desired.

All inventions, steps, processes, devices and methods described herein can be mixed and matched as desired. All previously described features, functions, or inventions described herein or by reference may be mixed and matched as desired.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A surgical device, comprising:
    a finger sheath configured to receive a portion of an index finger of a user, wherein the finger sheath includes a first end, a first end portion extending from the first end, the first end portion configured to receive the portion of the index finger, a second end and a second end portion extending from the second end and separated from the first end and the first end portion, wherein the second end portion includes an open region configured to allow for tactile feedback to the portion of the index finger;
    a flexible shaft having a first end, a second end and a lumen extending from the first end to the second end of the flexible shaft, wherein the flexible shaft is coupled to the finger sheath, wherein the flexible shaft is configured to permit access to tortuous anatomy by being flexible and configured to allow the user to traverse the tortuous anatomy of a patient;
    an anchor unit releasably coupled to the second end of the flexible shaft, wherein the anchor unit includes a lumen extending from a first end of the anchor unit to a second end of the anchor unit wherein the second end of the anchor unit extends past the second end of the finger sheath and is arranged under the finger sheath;
    a tissue anchor configured to be arranged in the lumen of the anchor unit; and
    an actuator configured to deliver the tissue anchor from the second end of the anchor unit upon operation.

2. The surgical device of claim 1, further comprising a suture attached to the tissue anchor.

3. The surgical device of claim 1, wherein the actuator includes a plunger actuation mechanism.

4. The surgical device of claim 1, wherein the open region of the finger sheath enables the index finger to palpate a tissue of the patient when the finger sheath is mounted on the index finger.

5. The surgical device of claim 4, wherein the second end of the anchor unit is configured to abut the tissue of the patient upon use when the finger sheath is mounted on the index finger and the index finger palpates the tissue.

6. The surgical device of claim 1, wherein the second end of the anchor unit is positioned below a back of a hand of the user when the finger sheath is mounted on the index finger.

7. A surgical device, comprising:
    a finger sheath configured to receive at least a portion of a finger of a user, the finger sheath including a first end portion configured to receive the portion of the finger and a second end portion separated from the first end portion, the second end portion including an open region;
    a flexible shaft having a first end, a second end, and a lumen extending from the first end to the second end;
    a flexible actuator at least partially arranged in the lumen of the flexible shaft, wherein the flexible actuator includes a first end and a second end; and
    a tubular member coupled to the second end of the flexible shaft, the tubular member including a lumen extending from a first end of the tubular member to a second end of the tubular member.

8. The surgical device of claim 7, wherein the tubular member extends along a side of the finger when the finger sheath is mounted on the finger.

9. The surgical device of claim 8, wherein the finger sheath includes an opening that enables the finger to palpate a tissue when the finger sheath is mounted on the finger.

10. The surgical device of claim 9, wherein the second end of the tubular member abuts the tissue when the finger sheath is mounted on the finger and the finger palpates the tissue.

11. The surgical device of claim 7, wherein the tubular member is configured to be positioned adjacent a hand of the user when the finger sheath is mounted on the finger.

12. A system, comprising:
    a tissue anchor;
    a suture material coupled to the tissue anchor;
    a flexible shaft having a first end, a second end, and a lumen extending from the first end to the second end;
    an actuator including a first end and a second end, the actuator is arranged within a lumen of the flexible shaft, wherein the actuator is flexible; and
    a finger assembly unit releasably coupled to the flexible shaft, the finger assembly unit comprising:
        a finger sheath including a first end portion configured to receive a portion of a finger and a second end portion separated from the first end portion, the second end portion defining an opening region that enables the finger to palpate a tissue, and
        a tubular member coupled to the finger sheath, the tubular member including a lumen extending from a first end of the tubular member to a second end of the tubular member, the lumen of the tubular member being configured to receive the actuator, the actuator being configured to deploy the tissue anchor from the second end of the tubular member into the tissue when the actuator is disposed within the lumen of the tubular member,
    wherein the second end of the flexible shaft is coupled the tubular member, and
    wherein the second end of the tubular member extends past a second end of the finger sheath.

13. The system of claim 12, wherein the actuator includes a plunger actuation mechanism.

14. The system of claim 13, wherein the flexible shaft comprises a thermoplastic material.

15. The system of claim 14, wherein the second end of the tubular member is configured to abut the tissue when the finger sheath is mounted on the finger and the index finger palpates the tissue.

16. The system of claim 12, wherein the tubular member is positioned below a hand of a user when the finger sheath is mounted on a finger of the user.

17. A surgical device, comprising:
    an elongate cylindrical housing, comprising a longitudinal lumen having a proximal opening and a distal opening and external walls, said external walls including a top wall, a bottom wall and first and second side walls, adapted for mounting on a finger of a user, wherein the distal opening is configured to allow for tactile feedback to a portion of the finger;

a tissue repair implant including a tissue anchor;

a guide tube comprising a lumen extending from a first end to a second end of the guide tube, wherein the guide tube is attached along a length of the elongate cylindrical housing, wherein the tissue repair implant is arranged in the lumen of the guide tube, and wherein the guide tube is configured for guiding the tissue repair implant out of the second end of the guide tube upon activation of an actuator; and a flexible shaft releasably coupled to the first end of the guide tube, wherein the flexible shaft is configured to permit access to tortuous anatomy by being flexible and configured to allow the user to traverse the tortuous anatomy of a patient, wherein the guide tube is attached to the elongate cylindrical housing such that a proximal opening of the guide tube is positioned adjacent a hand of the user when the elongate cylindrical housing is mounted on the finger, wherein the elongate cylindrical housing is configured so as to enable the user to palpate a tissue, through the distal opening of the elongate cylindrical housing, via the finger, to which the elongate cylindrical housing is configured to be attached, wherein the guide tube is attached along one of the first and second side walls of the elongate cylindrical housing such that the guide tube extends along a side of the finger when the elongate cylindrical housing is mounted on the finger, and wherein the guide tube is attached to the elongate cylindrical housing such that the proximal opening of the guide tube protrudes beyond a proximal end of the elongate cylindrical housing.

18. The device of claim 17, wherein the flexible shaft comprises a material selected from the group consisting of polyesters, polyurethanes, polyamides, polyolefins, polyethylene and polypropylene, and any copolymers thereof.

19. The device of claim 17, wherein the guide tube is attached to the elongate cylindrical housing such that the distal opening of the guide tube is displaced from the tissue when the finger of the user contacts the tissue.

20. The device of claim 17, wherein the tissue repair implant comprises a suture attached to the tissue anchor.

21. The device of claim 17, wherein the tissue is a posterior-lateral vaginal wall and the elongate cylindrical housing is configured for delivery into a vaginal canal via the finger.

22. The device of claim 21, wherein when the elongate cylindrical housing is positioned within the vaginal canal with the finger in contact with the posterior-lateral vaginal wall, the proximal opening of the guide tube extends out of the vaginal canal.

23. The device of claim 17, wherein the tissue repair implant is a mesh, a sling, a suture or a suture-anchor.

\* \* \* \* \*